US012808847B2

(12) United States Patent
Cui et al.

(10) Patent No.: US 12,808,847 B2
(45) Date of Patent: Nov. 24, 2026

(54) NONDESTRUCTIVE DETECTION SYSTEM AND METHOD FOR INTERNAL DEFECT OF FRUIT

(71) Applicant: ZHEJIANG UNIVERSITY, Zhejiang (CN)

(72) Inventors: Di Cui, Zhejiang (CN); Chengqiao Ding, Zhejiang (CN); Dachen Wang, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 509 days.

(21) Appl. No.: 18/556,357

(22) PCT Filed: Dec. 7, 2022

(86) PCT No.: PCT/CN2022/137242
§ 371 (c)(1),
(2) Date: Oct. 20, 2023

(87) PCT Pub. No.: WO2023/138247
PCT Pub. Date: Jul. 27, 2023

(65) Prior Publication Data

US 2024/0361276 A1 Oct. 31, 2024

(30) Foreign Application Priority Data

Jan. 20, 2022 (CN) ......................... 202210066516.0

(51) Int. Cl.
*G01N 29/06* (2006.01)
*G01N 29/24* (2006.01)
(Continued)

(52) U.S. Cl.
CPC ....... *G01N 29/069* (2013.01); *G01N 29/2418* (2013.01); *G01N 29/4418* (2013.01);
(Continued)

(58) Field of Classification Search
CPC ............. G01N 29/069; G01N 29/2418; G01N 29/4418; G01N 29/4481; G01N 33/025;
(Continued)

(56) References Cited

FOREIGN PATENT DOCUMENTS

CN 101603927 12/2009
CN 103308423 A * 9/2013
(Continued)

OTHER PUBLICATIONS

Abasi, Sadjad, et al. "Rapid measurement of apple quality parameters using wavelet de-noising transform with Vis/NIR analysis." Scientia horticulturae 252 (2019): 7-13. (Year: 2019).*
(Continued)

*Primary Examiner* — Yossef Korang-Beheshti
*Assistant Examiner* — Carter W Ferrell
(74) *Attorney, Agent, or Firm* — JCIPRNET

(57) ABSTRACT

Disclosed are a nondestructive detection system and a method for an internal defect of a fruit. The system comprises an aluminum profile frame, a conveyor belt, a tray, a pulse type gas spray device, and a laser Doppler vibrometer; when a piece of fruit passes a detection station, the pulse type gas spray device excites the fruit to vibrate, and the laser Doppler vibrometer evaluates a vibration response signal of the fruit; a time-domain vibration characteristic parameter and a frequency-domain vibration characteristic parameter are acquired by means of a wavelet transform and a fast Fourier transform; and a prediction model for an internal defect of the fruit is established on the basis of the acquired time-domain and frequency-domain vibration characteristic parameters.

6 Claims, 1 Drawing Sheet

(51) Int. Cl.

| | |
|---|---|
| ***G01N 29/44*** | (2006.01) |
| ***G01N 29/46*** | (2006.01) |
| ***G01N 33/02*** | (2006.01) |
| ***G06F 17/14*** | (2006.01) |

(52) U.S. Cl.
CPC ......... *G01N 29/4481* (2013.01); *G01N 29/46* (2013.01); *G01N 33/025* (2013.01); *G06F 17/148* (2013.01); *G06F 2218/06* (2023.01); *G06F 2218/08* (2023.01)

(58) Field of Classification Search
CPC ........ G01N 29/46; G01N 19/08; G01N 3/044; G01N 29/045; G01N 29/14; G01N 29/12; G01N 29/04; G06F 17/148; G06F 2218/06; G06F 17/18; G06F 2218/08; G06F 2218/12; B07C 5/34; G01H 9/00
See application file for complete search history.

(56) References Cited

FOREIGN PATENT DOCUMENTS

| | | | |
|---|---|---|---|
| CN | 109932333 A * | 6/2019 | |
| CN | 110865158 | 3/2020 | |
| CN | 110865158 A * | 3/2020 | ........... G01N 33/025 |
| CN | 111855800 | 10/2020 | |
| CN | 214251799 | 9/2021 | |
| CN | 114563347 | 5/2022 | |
| JP | 2000097920 | 4/2000 | |

OTHER PUBLICATIONS

Singh, Chandra B., et al. "Wavelet analysis of signals in agriculture and food quality inspection." Food and Bioprocess Technology 3.1 (2010): 2-12. (Year: 2010).*

Ying, Yibin B., et al. "Effect of wavelet transform techniques upon the estimation of sugar content in apple with near-infrared spectroscopy." Nondestructive sensing for food safety, quality, and natural resources. vol. 5587. SPIE, 2004. (Year: 2004).*

Ding Chengqiao, "Online nondestructive detection methods for firmness and hollow defect of watermelon based on acoustic vibration technology", Doctoral Thesis, College of Biosystems Engineering and Food Science, Zhejiang University, Nov. 2021, submit with English abstract, pp. 1-153.

"International Search Report (Form PCT/ISA/210) of PCT/CN2022/137242," mailed on Feb. 20, 2023, with English translation thereof, pp. 1-6.

* cited by examiner

NONDESTRUCTIVE DETECTION SYSTEM AND METHOD FOR INTERNAL DEFECT OF FRUIT

CROSS-REFERENCE TO RELATED APPLICATION

This application is a 371 of international application of PCT application serial no. PCT/CN2022/137242, filed on Dec. 7, 2022, which claims the priority benefit of China application no. 202210066516.0, filed on Jan. 20, 2022. The entirety of each of the above mentioned patent applications is hereby incorporated by reference herein and made a part of this specification.

TECHNICAL FIELD

The disclosure relates to the field of non-destructive detection, in particular to a non-destructive detection system and method for internal defects of fruits.

DESCRIPTION OF RELATED ART

The internal defects of the fruit will reduce the quality of the fruit and affect the consumers' intention to purchase. How to quickly and accurately identify the internal defects of the fruit is an issue that needs to be solved urgently. At present, the internal quality inspection of fruits in China mainly relies on the growers' experiences to make judgment by means of eye observation and listening to knocking sounds. Such manual method is not only time-consuming and labor-intensive, but also has low accuracy, and cannot meet the needs of high-throughput rapid and accurate detection. Therefore, it is urgent to construct a detection system for objective non-destructive detection of internal defects of fruits.

As a non-contact measurement method, laser Doppler vibration detection technology has the advantages of high sensitivity, fast dynamic response, and large measurement range. Such method is able to quickly, accurately and non-contact collect the vibration information of fruits. Since the vibration information of fruit is closely related to its mechanical and physical properties, laser Doppler vibrometer technology has the potential to detect internal defects of fruits.

The conventional fruit vibration data analysis method is to use the fast Fourier transform to convert the collected fruit vibration signal from the time-domain to the frequency-domain, extract the frequency-domain vibration characteristic parameters from the amplitude spectrum and phase spectrum, and establish a prediction model for inspecting the internal quality of the fruits based on these characteristic parameters. Although this method is simple and easy to implement, the online detection of internal defects in fruits is not accurate.

SUMMARY

In order to solve the problems existing in the background technology, the present disclosure provides a non-destructive detection system and method for fruit internal defects based on wavelet transformation. The designed pulse type gas spray device is adopted to excite the sample, and a laser Doppler vibrometer is adopted to collect the vibration response signal of the sample. In addition, wavelet transform is adopted to analyze the original vibration response signal in the time-frequency-domain, and the vibration characteristic parameters are extracted to establish a prediction model for internal defects of the fruits.

In order to realize the above functions, the present disclosure adopts the following technical solutions:

The present disclosure includes an aluminum profile frame, a conveyor belt, a tray, a pulse type gas spray device and a laser Doppler vibrometer. The conveyor belt is horizontally arranged on the upper end surface of the aluminum profile frame along the fruit-conveying direction, and a detection station is arranged in the middle of the conveyor belt. The pulse type gas spray device and the laser Doppler vibrometer are respectively provided on both sides of the detection station. The tray is transported on the conveyor belt, and fruits are placed on the tray.

The pulse type gas spray device includes a vertical frame, an air pump, an oil-water separator, a stepper motor, a stainless steel screw rod, a moving slider, an air nozzle and a solenoid valve. The vertical frame is located on one side of the detection station, the stepper motor body is fixed on the upper end surface of the vertical frame. The output shaft of the stepper motor is coaxially connected to the vertical stainless steel screw rod through a coupling. The middle part of the stainless steel screw rod is threaded with a moving slider. There is a vertical guide rod movably sleeved on both sides of the moving slider. The guide rod is fixed and vertically arranged between the bottom and the top of the vertical frame, thereby forming a lead screw nut sliding pair.

An air nozzle is provided on a side of the moving slider facing the detection station. The output end of the air pump is connected to the air nozzle through an oil-water separator, a solenoid valve, and an internal channel of the moving slider.

The disclosure further includes a lifting platform, which is set at the lower end of the laser Doppler vibrometer and fixedly arranged on the aluminum profile frame.

One end of the aluminum profile frame is provided with a transmission device. The transmission device includes a transmission shaft and a stepper motor. The transmission shaft passes through a rear end of the aluminum profile frame and is drivingly connected to the conveyor belt, and the body of the stepper motor is fixedly arranged on the aluminum profile frame, the other end of the transmission shaft is connected to the output shaft of the stepping motor through a belt.

The disclosure further includes a PLC controller, and a photoelectric sensor is arranged beside the detection station: the stepping motor, the electromagnetic valve, the laser Doppler vibrometer, and the photoelectric sensor are all electrically connected to the PLC controller.

The method adopts a non-destructive detection system for internal defects of fruits. The fruits may be watermelons, kiwis, plums, cherries, etc. The internal defects of the fruits are defined as defects of whether they are hollow. The method includes the following steps:

S1. When the fruit samples are transported to the detection station, a pulse type gas spray device is adopted to spray high-pressure air on the fruit samples to excite the fruit samples, and the laser Doppler vibrometer is adopted to collect the original vibration response signals of the fruit samples.

S2. Wavelet transform processing is performed on the original vibration response signal, time-domain and frequency-domain vibration characteristic parameters are extracted, and a prediction model is established.

S3. The prediction model is adopted to detect the fruits to be tested, and the hollow fruits are filtered.

The step S2 is specifically as follows:

S2.1. First, a Daubechies wavelet db5 is used for the original vibration response signal and the number of decomposition layers j is 5 for wavelet transform denoising processing. Then 13 time-domain vibration characteristic parameters are extracted from the vibration response signal after wavelet transform denoising, mainly including an average value $X_{mean}$, an average amplitude $X_{arv}$, a root mean square $X_{rms}$, a peak-to-peak value $X_{peak}$, a variance $s^2$, a skewness coefficient $S_k$, a kurtosis $K_u$, a shape factor W, a pulse factor I, a peak factor C, a margin factor M, an attenuation coefficient $\alpha$ and a waveform index $\beta$.

S2.2. The filter function of wavelet transform is used again to filter the 13 time-domain vibration characteristic parameters, specifically: the number of decomposition layers j in the wavelet transform is adjusted to obtain the approximate coefficient $a_j$ within the specified frequency range, and the approximate coefficient $a_j$ uses fast Fourier transform to obtain the frequency-domain vibration response signal, and then 5 preliminary frequency-domain vibration characteristic parameters are extracted from the frequency-domain vibration response signal, mainly including the second to fourth order resonant frequencies $f_2$, $f_3$ and $f_4$, the second-order resonance frequency amplitude $A_2$ and frequency band amplitude $BM_{85-160}$ between 85 Hz to 160 Hz.

S2.3. A part of the frequency-domain vibration characteristic parameters are adopted to eliminate the influence of the fruit sample mass on the resonance frequency according to the following calculation formula.

$$f_{in} = (m/m_0)^{1/3} f_i$$

In the formula, $f_{in}$ is the i-th order standardized resonance frequency; m is the sample mass; $m_0$ is a fixed mass; $f_i$ is the i-th order resonance frequency obtained by harmonic response analysis, where i=2, 3, 4.

Five frequency-domain vibration characteristic parameters are composed of three standardized resonance frequencies and the second-order resonance frequency amplitude $A_2$ and frequency band amplitude $BM_{85-160}$ among the five preliminary frequency-domain vibration characteristic parameters.

S2.4. The steel ball landfill method is adopted to measure the hollow volume of the fruit, and calculate the hollow rate H.

First, the fruit is cut along the equatorial plane, and steel balls with a diameter of 1 mm are continuously filled in the hollow part of the fruit sample until the hollow part is fully filled and aligned with the equatorial plane of the fruit sample. The total volume $V_0$ of the filled steel balls is calculated, fruit samples without hollow parts will not be filled. The total volume $V_0$ of the steel ball of the fruit sample without the hollow part is 0. The calculation formula for the hollow rate H of fruit samples is as follows:

$$H = V_0 / V_{sample\,volume}$$

S2.5. The original data set composed of 13 time-domain vibration characteristic parameters and 5 frequency-domain vibration characteristic parameters of all fruit samples is divided into a correction set and a verification set according to 2:1 through the sample set division method SPXY algorithm based on X-Y distance. According to the stepwise multiple linear regression method, part of the vibration characteristic parameters are screened from the time-domain and frequency-domain vibration characteristic parameters and used as the independent variables of the prediction model, and then different modeling methods are adopted to establish multiple different prediction models based on the correction set in sequence. Thereafter, the advantages and disadvantages of the multiple prediction models established are verified based on the verification set in turn.

The different modeling methods mentioned are stepwise multiple linear regression method, partial least squares regression method and BP neural network regression analysis method.

When the tray containing the fruit to be tested is transported to the detection station by the conveyor belt, the height of the air nozzle and the laser Doppler vibrometer probe are adjusted to the equatorial plane of the fruit to be tested through the stepper motor and lifting platform respectively. The photoelectric sensor is used to transmit the position signal to the PLC controller, and drive the pulse type gas spray device to spray high-pressure air on the fruit to be tested to excite the fruit to be tested. In the meantime, a laser Doppler vibrometer is adopted to collect the vibration response signal of the fruit to be tested.

Then the collected original vibration response signal is processed in the same method as the wavelet transform denoising in step S2 and the filter function of wavelet transform to obtain the time-domain and frequency-domain vibration characteristic parameters, and then the prediction model is used to obtain the hollow rate H of the fruit to be tested based on the time-domain and frequency-domain vibration characteristic parameters, and finally the hollow fruits are screened out.

Compared with existing technologies and methods, the present disclosure has the following advantages and benefits.

The data analysis method based on wavelet transform under the system of the present disclosure performs time-domain and frequency-domain analysis on the original vibration response signal, and extracts the time-domain and frequency-domain vibration characteristic parameters of the detected samples as independent variables of the prediction model, thereby improving the accuracy of the prediction model.

The disclosure has a simple operation process, may be applied to detect internal defects of other fruits, and has the characteristics of rapidity, efficiency, accuracy and so on.

DESCRIPTION OF THE EMBODIMENTS

The preferred embodiments of the present disclosure will be described in detail below in conjunction with the accompanying drawings, so that the advantages and features of the present disclosure can be more easily understood by those skilled in the art, so as to define the protection scope of the present disclosure more clearly.

Figure 1:
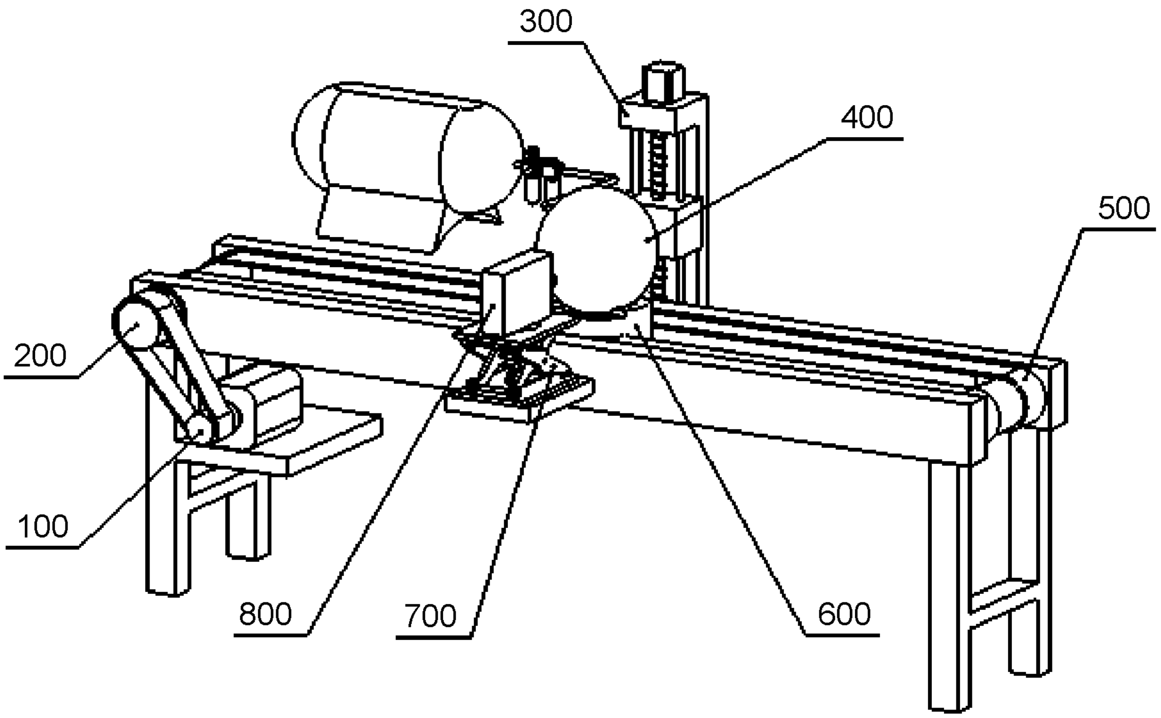
FIG. 1 is a schematic diagram of the overall structure of the present disclosure.

As shown in FIG. 1, the detection system of the present disclosure includes an aluminum profile frame, a conveyor belt 500, a tray 600, a pulse type gas spray device 300 and a laser Doppler vibrometer 800. The conveyor belt 500 is horizontally arranged on the upper end surface of the aluminum profile frame along the fruit-conveying direction, and a detection station is arranged in the middle of the conveyor belt 500. The pulse type gas spray device 300 and the laser Doppler vibrometer 800 are respectively provided on both sides of the detection station. The tray 600 is transported on the conveyor belt 500, and fruits 400 are placed on the tray 600.

Figure 2:
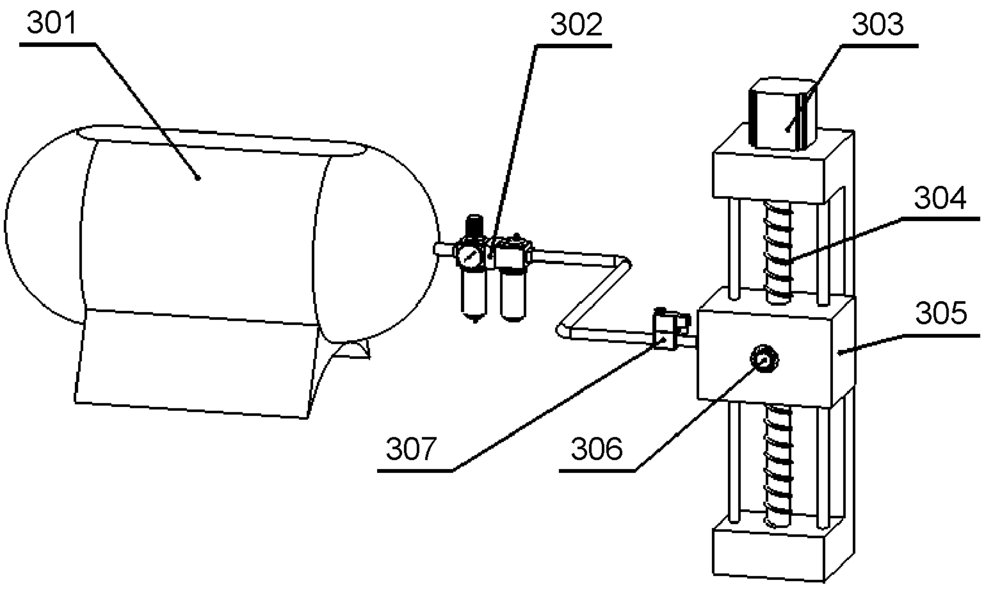
FIG. 2 is a schematic structural diagram of a gas spray excitation device.

As shown in FIG. 2, the pulse type gas spray device 300 of this detection system includes a vertical frame, an air pump 301, an oil-water separator 302, a stepper motor 303, a stainless steel screw rod 304, a moving slider 305, an air nozzle 306 and a solenoid valve 307. The vertical frame is located on one side of the detection station. The body of the stepper motor 303 is fixed on the upper end surface of the vertical frame. The output shaft of the stepper motor 303 is connected with a coupling. The output shaft of the stepper motor 303 is coaxially connected to a vertical stainless steel screw rod 304 through the coupling in the manner of facing downward. The stainless steel screw rod 304 is vertically and rotatably arranged in the vertical frame. The middle part of the stainless steel screw rod 304 is threaded with a moving slider 305. A vertical guide rod is movably sleeved on both sides of the moving slider 305. The guide rod is fixed and vertically arranged between the bottom and the top of the vertical frame, thereby forming a screw nut sliding pair. The stepper motor 303 is driven to drive the stainless steel screw rod 304 to rotate and thereby drive the moving slider to move up and down.

There is an air nozzle 306 on one side of the moving slider 305 facing the detection station. The output end of the air pump 301 is connected to the air nozzle 306 through the oil-water separator 302, the solenoid valve 307, and the internal channel of the moving slider 305. The air flow pressure is adjusted by the oil-water separator 302, and the opening and closing of the air nozzle 306 is controlled by the solenoid valve 307.

As shown in FIG. 1, the detection system also includes a lifting platform 700. The lifting platform 700 is set at the lower end of the laser Doppler vibrometer 800 and is fixedly arranged on the aluminum profile frame: the lifting platform 700 is adopted to adjust the height of the laser Doppler Vibrometer 800.

One end of the aluminum profile frame is provided with a transmission device. The transmission device includes a transmission shaft 200 and a stepper motor 100. The transmission shaft 200 passes through a rear end of the aluminum profile frame and is drivingly connected to the conveyor belt 500. The body of the stepper motor 100 is fixedly arranged on the aluminum profile frame. The other end of the transmission shaft 200 is drivingly connected to the output shaft of the stepper motor 100 through a belt. Therefore, the stepper motor 100 drives the transmission shaft 200 to drive the conveyor belt 500 to move.

The detection system further includes a PLC controller, and a photoelectric sensor is arranged next to the detection station: the stepper motor 303, the solenoid valve 307, the laser Doppler vibrometer 800, and the photoelectric sensor are all electrically connected to the PLC controller.

The fruits involved in specific implementation are watermelons, kiwis, plums, cherries, etc. The internal defects of the fruits are defined as whether they are hollow.

The detection method of the detection system will be described in detail with reference to the embodiments. The present embodiment selects 108 Kirin watermelons as experimental samples.

The steps of this detection method are as follows:

S1. When the watermelon fruit 400 sample is transported to the detection station, a pulse type gas spray device 300 is adopted to spray a high-pressure air onto the watermelon fruit 400 sample to excite the watermelon fruit 400 sample, and a laser Doppler vibrometer 800 is adopted to collect the original vibration response signal of the watermelon fruit 400 sample.

S2. Wavelet transform processing is performed on the original vibration response signal, time-domain and frequency-domain vibration characteristic parameters are extracted, and a prediction model is established.

S3. The prediction model is adopted to detect watermelons of fruits 400 to be tested, and hollow watermelon fruits are screened.

Step S2 is specifically as follows:

S2.1. First, a Daubechies wavelet db5 is used for the original vibration response signal and the number of decomposition layers j is 5 for wavelet transform denoising processing. Then 13 time-domain vibration characteristic parameters are extracted from the vibration response signal after wavelet transform denoising, mainly including an average value $X_{mean}$, an average amplitude $X_{arv}$, a root mean square $X_{rms}$, a peak-to-peak value $X_{peak}$, a variance $s^2$, a skewness coefficient $S_k$, a kurtosis $K_u$, a shape factor W, a pulse factor I, a peak factor C, a margin factor M, an attenuation coefficient α and a waveform index β. Please see Table 1.

TABLE 1

Calculation formulas of time-domain vibration characteristic parameters

| Time-domain vibration characteristic parameters | Calculation formula | Time-domain vibration characteristic parameters | Calculation formula |
|---|---|---|---|
| Average value | $X_{mean} = \frac{1}{n}\sum_{i=1}^{n} x_i^a$ | Form factor | $W = X_{rms}/X_{arv}$ |
| Average amplitude | $X_{arv} = \frac{1}{n}\sum_{i=1}^{n} \lvert x_i \rvert$ | Impulse factor | $I = X_{peak}/X_{arv}$ |

TABLE 1-continued

Calculation formulas of time-domain vibration characteristic parameters

| Time-domain vibration characteristic parameters | Calculation formula | Time-domain vibration characteristic parameters | Calculation formula |
|---|---|---|---|
| Root mean square | $X_{rms} = \sqrt{\frac{1}{n}\sum_{i=1}^{n}(x_i)^2}$ | Crest factor | $C = X_{peak}/X_{rms}$ |
| Peak to peak | $X_{peak} = \max(x_i) - \min(x_i)$ | Margin factor | $M = X_{peak} \Big/ \left(\frac{1}{n}\sum_{i=1}^{n}\sqrt{\lvert x_i\rvert}\right)^2$ |
| Variance | $s^2 = \frac{\sum_{i=1}^{n}(x_i - \overline{x})^2}{n-1}$ | Attenuation coefficient | $f(t) = Ae^{-\alpha(t-t0)}$ |
| Skewness coefficient | $S_k = \frac{\sum_{i=1}^{n}(x_i - \overline{x})^3/n}{s^3}$ | Form index | $\beta = \lvert\max(x_i)/\min(x_i)\rvert$ |
| Kurtosis | $K_u = \frac{\sum_{i=1}^{n}(x_i - \overline{x})^4/n}{s^4} - 3$ | | |

In the table: a xi is the data value of the time-domain vibration response signal; n is the number of data points of the time-domain vibration response signal; s is the standard deviation.

S2.2. The filter function of wavelet transform is used again to filter the 13 time-domain vibration characteristic parameters. The number of decomposition layers j is adjusted to obtain the approximate $\text{coefficient}_j$ within the specified frequency range, and fast Fourier transform is adopted on the approximate $\text{coefficient}_j$ to obtain the frequency-domain vibration response signal, and then 5 preliminary frequency-domain vibration characteristic parameters are extracted from the frequency-domain vibration response signal, mainly including the second to fourth order resonant frequencies $f_2$, $f_3$ and $f_4$, the second-order resonance frequency amplitude $A_2$ and frequency band amplitude $BM_{85\text{-}160}$ between 85 Hz to 160 Hz. Specifically, the filter function of wavelet transform is that wavelet transform fixes the analyzed frequency-domain signal in a certain frequency band by adjusting the number of decomposition layers, which serves a function similar to a bandpass filter. Specifically, in the fitting process of wavelet transform, every time the number of decomposition layers j is increased, the wavelet coefficients will be reduced by half, and the frequency range will become half as compared with the original frequency range. Therefore, the analyzed frequency-domain signal may be fixed at a certain frequency band by adjusting the number of decomposition layers.

S2.3. A part of the frequency-domain vibration characteristic parameters is adopted to eliminate the influence of the watermelon fruit 400 sample mass on the resonance frequency according to the following calculation formula:

$$f_{in} = (m/m_0)^{1/3} f_i$$

In the formula, $f_{in}$ is the i-th order standardized resonance frequency; m is the sample mass; $m_0$ is 100 g; $f_i$ is the i-th order resonant frequency obtained by harmonic response analysis, where i=2, 3, 4.

Five frequency-domain vibration characteristic parameters are composed of three standardized resonance frequencies, the second-order resonance frequency amplitude $A_2$ in the five preliminary frequency-domain vibration characteristic parameters, and the frequency band amplitude $BM_{85\text{-}160}$ between 85 Hz to 160 Hz.

S2.4. The steel ball filling method is adopted to measure the hollow volume of watermelon fruit and calculate the hollow rate H:

First, the watermelon fruit is cut along the equatorial plane, and steel balls with a diameter of 1 mm are continuously filled in the hollow part of the watermelon fruit 400 sample until the hollow part is fully filled and aligned with the equatorial plane of the watermelon fruit 400 sample. The total volume, which is denoted as $V_0$, of the filled steel balls is calculated, watermelon fruit 400 samples without hollow parts will not be filled. The total volume $V_0$ of the steel ball of the watermelon fruit 400 sample without the hollow part is 0. The calculation formula for the hollow rate H of the watermelon fruit samples is as follows:

$$H = V_0/V_{sample\,volume}$$

S2.5. The original data set composed of 13 time-domain vibration characteristic parameters and 5 frequency-domain vibration characteristic parameters of all watermelon fruit (400) samples is divided into a correction set and a verification set according to 2:1 through the sample set division method SPXY algorithm based on X-Y distance. According to the stepwise multiple linear regression method, part of the vibration characteristic parameters are screened from the time-domain and frequency-domain vibration characteristic parameters and used as the independent variables of the prediction model, and then different modeling methods are adopted to establish multiple different prediction models based on the correction set in sequence. Thereafter, the advantages and disadvantages of the multiple prediction models established are verified based on the verification set in turn.

The different modeling methods are stepwise multiple linear regression method, partial least squares regression method and BP neural network regression analysis method. Among them, the hidden layer and output layer activation functions of the BP neural network regression analysis method are selected as tangent-sigmoid function and purelin function respectively, and the learning efficiency and error range are set to 0.1 and 0.0004 respectively.

Step S3 is specifically as follows:

When the tray 600 containing the watermelon fruit 400 to be tested is transported to the detection station by the conveyor belt 500, the height of the air nozzle and the probe of the laser Doppler vibrometer 800 are adjusted to the equatorial plane of the watermelon fruit 400 to be tested through the stepping motor 303 and the lifting platform 700 respectively. The pulse width of the pulse type gas spray device 300 is set to 200 ms, the oil-water separator 302 is utilized to adjust the air pressure to 250 kPa: the photoelectric sensor is adopted to transmit the position signal to the PLC controller, and drive the pulse type gas spray device 300 to spray high-pressure air to the watermelon fruit 400 to be tested to excite the watermelon fruit 400 to be tested. In the meantime, a laser Doppler vibrometer 800 is adopted to collect the vibration response signal of the watermelon fruit 400 to be tested.

Then the collected original vibration response signal is processed in the same method as the wavelet transform denoising in step S2 and the filter function of wavelet transform to obtain the time-domain and frequency-domain vibration characteristic parameters, and then the prediction model is adopted to obtain the hollow rate H of watermelon fruits 400 to be tested according to the time-domain and frequency-domain vibration characteristic parameters. Finally, the hollow fruits are screened. In the present embodiment, the hollow rate of watermelon fruit 400 to be tested is specifically shown in Table 2.

TABLE 2

Sample number and hollow rate statistics of the calibration set and validation set of the watermelon internal hollow defect prediction model (n = 108)

| Sample set | Number of samples | Range of hollow rate | Average of hollow rate | Standard deviation of hollow rate |
|---|---|---|---|---|
| Correction set | 72 | 0.000-0.102 | 0.018 | 0.030 |
| Verification set | 36 | 0.000-0.097 | 0.016 | 0.026 |

In order to avoid the collinearity problem between the independent variables, when setting up the multivariate regression model, first the stepwise multiple linear regression method is adopted to screen the better variable combination. 10 independent variables are screened in this embodiment, which are $X_{mean}$, $K_u$, W, I, C, M, α, β, $f_{2n}$, and $BM_{85\text{-}160}$ respectively. Then, stepwise multiple linear regression method, partial least squares regression method, and BP neural network regression analysis method are adopted in sequence to establish a prediction model for hollow defects in watermelon. The results are shown in Table 3.

TABLE 3

Prediction model results of hollow defects in watermelon (n = 108)

| Modeling method | Input variables | Correction set (n = 72) $r_c$ | Correction set (n = 72) RMSEC | Verification set (n = 36) $r_p$ | Verification set (n = 36) RMSEP |
|---|---|---|---|---|---|
| Stepwise multiple linear regression | 10 variables[a] | 0.860 | 0.013 | 0.814 | 0.014 |
| Partial least squares regression | | 0.841 | 0.017 | 0.807 | 0.018 |
| BP neural network regression | | 0.893 | 0.010 | 0.829 | 0.016 |

Note:
[a]The 10 independent variables are $X_{mean}$, $K_u$, W, I, C, M, α, β, $f_{2n}$, $BM_{85\text{-}160}$.

As can be seen from Table 3, it is feasible to use the data analysis method based on wavelet transform to extract time-domain and frequency-domain vibration characteristic parameters to predict hollow watermelons. In addition, each module of the above-mentioned non-destructive detection system has certain adjustability and may be used to detect internal defects of other fruits.

What is claimed is:

1. A nondestructive detection system for an internal defect of a fruit, comprising an aluminum profile frame, a conveyor belt, a tray, a pulse type gas spray device and a laser Doppler vibrometer; wherein the conveyor belt is horizontally arranged on an upper end surface of the aluminum profile frame along a fruit-conveying direction, and a detection station is arranged in a middle of the conveyor belt, the pulse type gas spray device and the laser Doppler vibrometer are respectively provided on opposite sides of the detection station; the tray is transported on the conveyor belt, and fruits are placed on the tray;

wherein the pulse type gas spray device comprises a vertical frame, an air pump, an oil-water separator, a stepper motor, a stainless steel screw rod, a moving slider, an air nozzle and a solenoid valve; the vertical frame is located on a side of the detection station, a body of the stepper motor is fixed on an upper end surface of the vertical frame, an output shaft of the stepper motor is coaxially connected to the stainless steel screw rod through a coupling in a manner of facing downward, a middle part of the stainless steel screw rod is threaded with the moving slider, two vertical guide rods are respectively movably sleeved on each of two sides of the moving slider, the vertical guide rods are fixed and vertically arranged between a bottom of the vertical frame and a top of the vertical frame, thereby forming a screw nut sliding pair;

the air nozzle is disposed on one side of the moving slider facing the detection station, an output end of the air pump is connected to the air nozzle through the oil-water separator, the solenoid valve, and an internal channel of the moving slider;

wherein a nondestructive detection method for the internal defect of the fruit adopts the nondestructive detection system, the internal defect of the fruit is defined as whether the fruit is hollow, comprising the following steps:

S1. when a fruit sample is transported to the detection station, the pulse type gas spray device is adopted to spray a high-pressure air onto the fruit sample to excite the fruit sample, and the laser Doppler vibrometer is adopted to collect an original vibration response signal of the fruit sample;

S2. a wavelet transform denoising processing is performed on the original vibration response signal, time-domain and frequency-domain vibration characteristic parameters are extracted, and a prediction model is established;

S3. the prediction model is adopted to detect the fruits to be tested, and hollow fruits are screened;

wherein the step S2 is specifically as follows:

S2.1. first, a Daubechies wavelet db5 is used for the original vibration response signal and a number of decomposition layers j is 5 for wavelet transform denoising processing, then 13 time-domain vibration characteristic parameters are extracted from a vibration response signal after the wavelet transform denoising processing, comprising an average value $X_{mean}$, an average amplitude $X_{arv}$, a root mean square $X_{rms}$, a peak-to-peak value $X_{peak}$, a variance $s^2$, a skewness coefficient $S_k$, a kurtosis $K_u$, a shape factor W, a pulse factor I, a peak factor C, a margin factor M, an attenuation coefficient a and a waveform index β;

S2.2. a filter function of the wavelet transform denoising processing is used again to filter the 13 time-domain vibration characteristic parameters, specifically: the number of decomposition layers j in the wavelet transform denoising processing is adjusted to obtain an approximate coefficient a within a specified frequency range, and a fast Fourier transform is adopted on the approximate coefficient $a_j$ to obtain a frequency-domain vibration response signal, and then 5 preliminary frequency-domain vibration characteristic parameters are extracted from the frequency-domain vibration response signal, comprising second to fourth order resonant frequencies $f_2$, $f_3$ and $f_4$, a second-order resonance frequency amplitude $A_2$ and a frequency band amplitude $BM_{85-160}$ between 85 Hz to 160 Hz;

S2.3. a part of the 5 preliminary frequency-domain vibration characteristic parameters is adopted to eliminate an influence of a mass of the fruit sample on a resonance frequency according to the following calculation formula:

$$f_{in} = (m/m_0)^{1/3} f_i$$

wherein $f_{in}$ is an i-th order standardized resonance frequency; m is a sample mass; $m_0$ is a fixed mass; $f_i$ is an i-th order resonant frequency obtained by a harmonic response analysis, wherein i=2, 3, 4;

5 frequency-domain vibration characteristic parameters are composed of three standardized resonance frequencies, the second-order resonance frequency amplitude $A_2$ in the 5 preliminary frequency-domain vibration characteristic parameters, and the frequency band amplitude $BM_{85-160}$;

S2.4. a steel ball filling method is adopted to measure a hollow volume of the fruit sample and calculate a hollow rate H:

first, the fruit sample is cut along an equatorial plane, and steel balls with a diameter of 1 mm are continuously filled in a hollow part of the fruit sample until the hollow part is fully filled and aligned with the equatorial plane of the fruit sample, a total volume $V_0$ of the filled steel balls is calculated, a calculation formula for the hollow rate H of the fruit sample is as follows:

$$H = V_0 / V_{sample\ volume},$$

wherein the $V_{sample\ volume}$ is a total volume of the fruit sample;

S2.5. an original data set composed of the 13 time-domain vibration characteristic parameters and the 5 frequency-domain vibration characteristic parameters of all fruit samples is divided into a correction set and a verification set through a sample set division method SPXY (Sample set Partitioning based on joint X-Y distances) algorithm based on an X-Y distance; a ratio of number of samples of the correction set and number of samples of the verification set is 2:1; according to a stepwise multiple linear regression method, a part of the time-domain and frequency-domain vibration characteristic parameters are screened from the time-domain and frequency-domain vibration characteristic parameters and used as independent variables of the prediction model, and multiple different prediction models are established based on the correction set in sequence according to different modeling methods.

2. The nondestructive detection system for the internal defect of the fruit according to claim 1, further comprising a lifting platform, wherein the lifting platform is set at a lower end of the laser Doppler vibrometer and is fixedly arranged on the aluminum profile frame.

3. The nondestructive detection system for the internal defect of the fruit according to claim 1, wherein one end of the aluminum profile frame is provided with a transmission device; the transmission device comprises a transmission shaft and an another stepper motor; the transmission shaft passes through an end of the aluminum profile frame and is drivingly connected to the conveyor belt, a body of the another stepper motor is fixedly arranged on the aluminum profile frame, an other end of the transmission shaft is drivingly connected to an output shaft of the another stepper motor through a belt.

4. The nondestructive detection system for the internal defect of the fruit according to claim 1, further comprising a PLC controller, wherein a photoelectric sensor is arranged next to the detection station; the stepper motor, the solenoid valve, the laser Doppler vibrometer, and the photoelectric sensor are all electrically connected to the PLC controller.

5. The nondestructive detection method for the internal defect of the fruit according to claim 1, wherein the different modeling methods are the stepwise multiple linear regression method, a partial least squares regression method and a BP neural network regression analysis method.

6. The nondestructive detection method for the internal defect of the fruit according to claim 1, wherein the step S3 is specifically as follows:

when the tray containing the fruits to be tested is transported to the detection station by the conveyor belt, heights of the air nozzle and a probe of the laser Doppler vibrometer are adjusted to the equatorial plane of the fruit to be tested through the stepping motor and a lifting platform respectively, a photoelectric sensor is adopted to transmit a position signal to a PLC controller, and drive the pulse type gas spray device to spray the high-pressure air to the fruits to be tested to excite the fruits to be tested, the laser Doppler vibrometer is adopted to collect the original vibration response signal of the fruits to be tested;

then the collected original vibration response signal is processed in the same method as the wavelet transform denoising processing in step S2 and the filter function of the wavelet transform denoising processing to obtain the time-domain and frequency-domain vibration characteristic parameters, and then the prediction model is adopted to obtain hollow rates H of the fruits to be tested according to the time-domain and frequency-domain vibration characteristic parameters, and finally the hollow fruits are screened.

* * * * *